(12) United States Patent
Wu et al.

(10) Patent No.: US 7,030,243 B1
(45) Date of Patent: Apr. 18, 2006

(54) PROCESS FOR MAKING CAMPTOTHECIN DERIVATIVES

(75) Inventors: Ye Wu, Helotes, TX (US); Kesavaram Narkunan, San Antonio, TX (US); Jianyan Wang, Helotes, TX (US); Harry Kochat, San Antonio, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 10/976,109

(22) Filed: Oct. 28, 2004

(51) Int. Cl.
*C07D 491/22* (2006.01)

(52) U.S. Cl. ...................................................... 546/48

(58) Field of Classification Search ................... 546/48
See application file for complete search history.

(56) References Cited

U.S. PATENT DOCUMENTS 6,194,579 B1    2/2001   Hausheer
6,723,849 B1    4/2004   Narkunan et al.

*Primary Examiner*—Bruck Kifle
(74) *Attorney, Agent, or Firm*—Akin Gump Strauss Hauer & Feld, LLP

(57) ABSTRACT

A process for synthesizing highly lipophilic derivatives of camptothecin. The process includes reacting dissolved, underivatized camptothecin with a silylated heterocyclic compound in a modified Minisci-type alkylation reaction to produce 7-substituted derivatives of camptothecin.

7 Claims, No Drawings

PROCESS FOR MAKING CAMPTOTHECIN DERIVATIVES

CROSS-REFERENCE TO RELATED APPLICATION

This application claims the benefit of U.S. Provisional Application No. 60/530,153, filed Dec. 17, 2003.

FIELD OF THE INVENTION

This invention relates to a process for making certain camptothecin derivatives and will have application to a semi-synthetic process for making large quantities of highly lipophilic camptothecins that include one or more silicon atoms in the structure.

BACKGROUND OF THE INVENTION

Highly lipophilic camptothecin derivatives (HLCDs), particularly those containing silicon-based moieties, are effective anticancer drugs. One of the most noted of the silicon-containing HLCDs has the IUPAC name (4S)-4-ethyl-4-hydroxy-11-[2-(trimethylsilyl)ethyl]-1H-pyrano[3':4':6,7]indolizino[1,2-b]quinoline-3,14(4H,12H)-dione, and has also referred to as 7-(2'-trimethylsilyl)ethyl camptothecin (also known as Karenitecin™ and BNP1350), currently in human clinical trials in the United States and internationally. U.S. Pat. No. 5,910,491 and others describe the compositions, formulations, and processes for making Karenitecin™ and other related HLCDs.

Currently known most preferred processes for making Karenitecin™ are described and claimed in U.S. Pat. No. 6,194,579 (the '579 patent), incorporated herein by reference, and in U.S. patent application Ser. No. 10/627,444, filed Jul. 25, 2003. In the '579 patent, Karenitecin™ and other silicon-containing HLCDs are manufactured by reacting camptothecin with a TMS-aldehyde and a strong oxidizing agent (hydrogen peroxide is preferred) in the presence of a metal sulfate to effect a Minisci-type alkylation. As described in the '579 patent, the resulting alkylation moiety contained one less carbon atom than the TMS-aldehyde, a typical characteristic of the Minisci alkylation.

The prior patented process for synthesizing Karenitecin was efficient in small-scale (laboratory-scale) production, but improvements were necessary to enable efficient larger scale production. Improvements were needed primarily to boost yields by optimizing process parameters and reagents of choice (and accordingly reduce impurities) and also in analytical methods to address the impurity profile of the active pharmaceutical ingredient (powder form BNP1350), and to simplify the purification process to make it user friendly and robust for manufacturing scale. The prior process resulted in a 50%–60% crude theoretical yield and a 25% to 35% isolated yield after column chromatography. The new process, disclosed herein, demonstrated approximately an 80% crude theoretical yield and a 45% to 50% isolated yield after double crystallization.

Other prior processes for synthesizing HLCDs can be found in U.S. Pat. No. 6,150,343 and others. These prior processes utilize a total synthesis route to synthesize the camptothecin skeleton. Due to the relatively low yields and higher costs of these methods when compared to semisynthetic methods, they are considered impractical and inefficient for conducting large-scale synthetic operations.

U.S. patent application Ser. No. 10/627,444, filed Jul. 25, 2003, referred to above describes and claims a modified process for synthesizing HLCDs. In the modified process disclosed in the '444 patent application, the main difference in the process was the addition of a nonpolar, aprotic solvent to the initial mixture of the trimethylsilyl aldehyde reactant in order to boost yields.

SUMMARY OF THE INVENTION

The synthetic process of this invention is adapted to produce HLCDs having the following structure I:

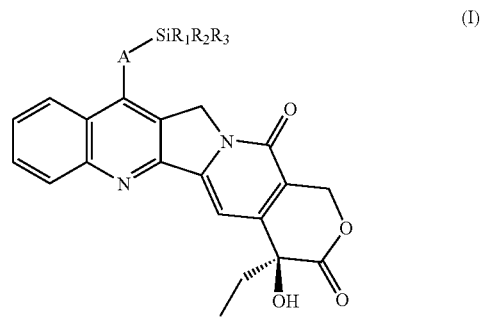

wherein A is —$(CH_2)_m$— where m is 1 to 6;
and $R_1$, $R_2$, and $R_3$ are individually lower alkyl or aryl.

The process is essentially a one-step process for synthesizing the preferred compounds from camptothecin. As is well known, camptothecin can be isolated from the bark of the *camptotheca accuminata* tree, which grows primarily in Asia and parts of Europe. The active form of camptothecin is the (S)-stereoisomer shown above, which can be purchased as a commercial product either in GMP grade or non-GMP grade with substantial purity from any of a number of commercial sources located primarily in China, India and Europe.

In the process of this invention, a modified Minisci alkylation is utilized to synthesize the formula I compound from unsubstituted camptothecin. Instead of a trimethylsilyl aldehyde as initial reactant, the process of this invention utilizes a trialkylsilyl-alkyl-cyclic compound as one of the key intermediates. The process of this invention boosts yields beyond those realized by the previous semisynthetic processes, and is efficient and economical in both small and large-scale process operations.

DETAILED DESCRIPTION OF THE INVENTION

The preferred embodiments depicted below are not intended to be exhaustive or to limit the invention to the precise forms disclosed. They have been chosen and described to explain the principles of the invention, and its application and practical use to thereby enable others skilled in the art to understand its teachings.

In this application, the term "lower alkyl" means a straight or branched chain hydrocarbon having from one to six total carbon atoms. "Lower alkylene" means a bridging hydrocarbon having from one to six total carbon atoms bonded at its terminal carbons to two other atoms, specifically (—$CH_2$—)$_x$, where x is 1 to 6. "Lower alcohol" likewise means an alcohol having from 1 to 6 total carbon atoms. "Aryl" means an aromatic ring system, fused or unfused, preferably from one to three total rings, with the ring elements consisting entirely of carbon atoms.

Examples of defined terms include, but are not limited to:

Lower alkyl-methyl, ethyl, propyl, isopropyl, butyl, isobutyl, tert-butyl, etc.

Lower alkylene-methylene, ethylene, propylene, isopropylene, butylene, etc.

Lower alcohol-methanol, ethanol, isopropanol, tert-butyl alcohol, etc.

Aryl-benzyl, phenyl, naphthyl, fluorenyl, and substituted derivatives, etc.

The process of this invention is employed to synthesize compounds of formula I, shown above. Preferred compounds synthesized by the process include those compounds where m is 1, 2 or 3, and $R_1$, $R_2$ and $R_3$ are methyl, tert-butyl or phenyl. The process is depicted in the following Schemes.

Scheme 1

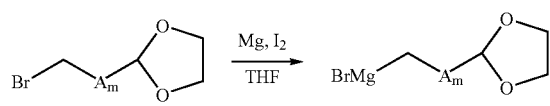

Scheme 1 illustrates the synthesis of an intermediate Grignard reagent used in forming the intermediate that will be reacted with camptothecin to synthesize the formula I compound. As shown in the illustration above, a bromoalkylene heterocyclic compound (illustrated, without limitation as 2-bromoethyl-1,3-dioxolane) is reacted in Grignard fashion with magnesium and iodine to form the Grignard reagent shown.

Scheme 2

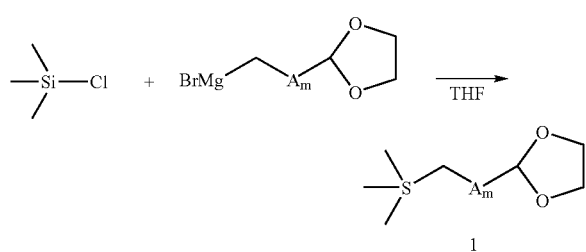

Scheme 2 illustrates the preparation of the silylated reactant from the corresponding Grignard reagent from Scheme 1. In the Scheme, m is 1 to 5 and the alkylene chain linking the terminal silane to the heterocycle may be straight chain or branched-chain, as desired. Preferably, m is 1 to 3, most preferably 1, and the most preferred end product is 2'-trimethylsilylethyl-1,3-dioxolane 1.

The process shown in Schemes 1 and 2 is preferably a one-step, single pot process. All reagents are generally available from commercial sources. As shown, chlorotrimethylsilane is reacted with the Grignard reagent, from Scheme 1, preferably in a nonpolar, aprotic solvent such as tetrahydrofuran (THF).

Scheme 3

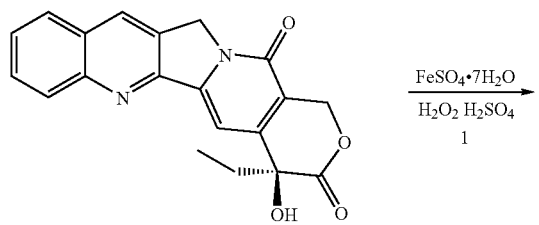

-continued

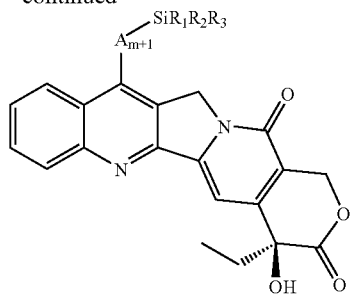

Scheme 3 illustrates the conversion of (S)-camptothecin to the desired formula I compound. The conversion is preferably achieved through the modified Minisci-type hemolytic alkylation reaction. A Minisci-type alkylation as shown above allows for substitution of the alkyl moiety to the scaffold with n–1 number of carbon atoms with respect to the reactant bearing "n" number of alkyl carbons.

In the process of this invention, as depicted in Scheme 3, the modified Minisci-type alkylation provides for dissolving the heterocyclic intermediate 1 from Scheme 2 in a suitable solvent, preferably with a low molecular weight pharmaceutically relevant solvent as suitable co-solvent. This solution is then added to a solution of camptothecin in a strong acid capable of protonating the N–1 moiety of camptothecin, and a metal sulfate. In prior processes utilized to synthesize the formula I compounds, the reactants tended to be unstable and resulted in low yields, partially due to the in situ generation of undesired by-product derived from the co-solvent.

After adding the heterocyclic intermediate 1 from Scheme 2 to the camptothecin solution, a strong oxidizing agent, preferably hydrogen peroxide, is slowly added to the mixture. The formula I compound is then isolated, filtered, washed and purified by recrystallization.

The following specific examples illustrate the process, but are not to be considered as limiting the invention to the precise reagents, steps or conditions depicted.

EXAMPLE 1

Synthesis of 2-(2-trimethylsilylethyl)-1,3-dioxolane

Equipment Preparation:

A jacketed glass reactor equipped with reflux condenser, overhead stirrer and dropping funnel was dressed up, so as to avoid any residual moisture. The glass reactor was purged with a stream of nitrogen prior to beginning the reaction process.

| Reagents and Other Chemicals Used: | |
|---|---|
| Anhydrous Tetrahydrofuran | = 400 mL |
| Magnesium Granules | = 10 grams (0.411 mol) |
| Trimethylsilyl chloride | = 36.8 mL (0.290 mol) |
| 2-Bromoethyl-1,3-dioxolane | = 50 grams (0.276 mol) |
| Iodine Crystals | = 100 mg (catalytic) |
| Methyl t-butyl ether | = 300 mL |
| Anhydrous Sodium sulfate | = 40 g |

Process Operation:

The reactor was charged with 400 mL of commercially available anhydrous tetrahydrofuran (THF) followed by 10 grams of magnesium granules to form a suspension of magnesium granules in anhydrous THF. To the above suspension was then introduced approximately 100 mg of iodine crystals. The completion of Grignard Reagent formation was visually inspected by insuring complete decoloration of iodine in the reaction medium. The contents were cooled to 0° C. to 5° C. using cold-water circulation. Once the reaction medium attained the desired temperature, 2-bromoethyl-1,3-dioxane was charged as a thin stream using an overhead-dropping funnel. The reaction mixture was then agitated for approximately 2 hours while allowing the reaction temperature to slowly rise to ambient temperature. The reaction mixture was then cooled back to 0° C. to 5° C. and then charged with trimethylsilyl chloride as a thin stream using the overhead-dropping funnel. The reaction mixture was allowed to attain ambient temperature and agitated overnight. Volatiles were then distilled off directly from the reactor. The remaining organic residue was then dissolved in 200 mL methyl t-butyl ether (MTBE) and filtered to remove magnesium bromide chloride and the excess magnesium granules. The reactor was washed down using another 100 mL of MTBE. The organic portions were combined and then charged back to the reactor, washed with 80 mL of process water, and the organic portion was dried over anhydrous sodium sulfate (40 grams), filtered and concentrated to obtain the desired crude product (30 grams). The crude product was then distilled between 65° C.–67° C. at 30 mm Hg reduced pressure to furnish 24.13 grams of 2-(2-trimethylsilylethyl)-1,3-dioxolane as colorless oil.

$^1$H NMR (300 MHz, CDCl$_3$) δ: −0.001 (9H, s), 0.56–0.62 (2H, m), 1.59–1.67 (2H, m), 3.84–4.00 (4H, m), 4.82 (1H, t, J=4.7 Hz).

EXAMPLE 2

Synthesis of 7-(2-trimethylsilylethyl) camptothecin (BNP1350)

Equipment Preparation:

A jacketed glass reactor equipped with reflux condenser, overhead stirrer and dropping funnel was dressed up.

| Reagents and Other Chemicals Used: | |
| --- | --- |
| Crystallized 20S-Camptothecin | = 1.3 g (3.73 mM) |
| 2-(2-trimethylsilylethyl)-1,3-dioxolane | = 1.56 g (8.95 mM) |
| 30% Hydrogen peroxide | = 1.04 mL |
| Ferrous sulfate heptahydrate | = 1.3 g |
| t-Butyl alcohol | = 26 mL |
| 30% Sulfuric acid | = 78 mL (Stock solution) |
| Cyclohexane | = 130 mL |
| Dichloromethane | = 130 mL |
| Anhydrous Sodium sulfate | = 20 g |
| N,N-dimethyl formamide | = 22 mL |
| Sodium sulfite | = 1.04 g |

Process Operation:

The reaction vessel was charged with 78 mL of 30% sulfuric acid. While agitating continued, 1.3 g of crystallized 20S-camptothecin and 1.3 g of ferrous sulfate heptahydrate were added at ambient temperature. Agitation was continued until both the components were completely dissolved in the aqueous sulfuric acid. To the above pale yellow/clear solution was charged as a thin stream using the overhead dropping funnel 1.56 g of 2-(2-trimethylsilylethyl)-1,3-dioxolane dissolved in 26 mL of t-butyl alcohol. After the addition was completed, the reaction medium was cooled to 15° C. using chilled water circulation. Once the reaction temperature had reached 15° C., addition of 1.04 mL of 30% hydrogen peroxide solution was started, in a manner ranging from drop-wise addition to a thin stream, through the dropping funnel while maintaining the reaction temperature between 15° C.–20° C. The reaction mixture was agitated for an additional 30 minutes at the same temperature. At the end of 30 minutes, the excess amount of hydrogen peroxide was quenched by adding 1.04 g of sodium sulfite. An in-process HPLC assay was done at this point to verify the progression of the reaction and the level of impurities formed.

The reactor containing the reaction mixture was charged with 130 mL of cyclohexane and the contents agitated for 20 minutes. The organic layer was allowed to separate. The cyclohexane portion was drained to a waste container. The reactor was then recharged with the aqueous layer. To the above aqueous reaction mixture was added 19.5 mL of cold process water to dilute the aqueous portion. The aqueous layer was then extracted twice with 65 mL of dichloromethane, with each extraction being performed with an agitation time of 15 minutes and standing time of 5 minutes. The aqueous layer was then drained into a waste container. The combined dichloromethane layer was then recharged into the reactor and the organic portion was washed with 26 mL of process water by agitation for 15 minutes. The water washing was drained into a waste container. The reactor was then charged with 20 g of anhydrous sodium sulfate. The resulting suspension was agitated for 15 minutes. The suspension was filtered through a 10-gram silica gel bed (60 to 100 micron size) to remove the sodium sulfate. The pale yellow organic layer thus obtained was then concentrated to obtain light brownish crude product (1.25 g; 74.7% crude yield; HPLC purity=94.8%).

The crude product was then suspended in 19.5 mL of ethyl alcohol and stirred for 10 minutes. The solid was filtered through a sintered funnel, washed once with 2.6 mL of ethyl alcohol, dried at 40° C. overnight under reduced pressure. The product was analyzed by HPLC and was found 96.9% pure by peak area and weighed to 1.06 g. The product thus obtained was further purified by recrystallizing from 11 mL of anhydrous N,N-dimethyl formamide. The product obtained after crystallization (0.928 g; 55.40% yield) was found 98.9% pure. The DMF recrystallization was repeated one more time to obtain 0.835 g (49.91% overall yield) of the desired product (BNP1350) with 99.12% purity.

$^1$H NMR (300 MHz, CDCl$_3$) δ; 0.18 (9H, s), 0.90–0.96 (2H, m), 1.04 (3H, t, J=7.4 Hz), 1.82–1.96 (2H, m), 3.08–3.14 (2H, m), 5.24(2H, s), 5.33(1H, d, J=16.5 Hz), 5.76 (1H, d, J=16.5 Hz), 7.64–7.69 (2H, m), 7.80 (1H, t, J=7.2 Hz), 8.04 (1H, d, J=8.4 Hz), 8.23 (1H, d, J=8.4 Hz); $^{13}$C NMR (75 MHz, CDCl$_3$) δ; −1.63, 8.08, 17.99, 24.35, 31.80, 49.47, 66.54, 72.99, 98.35, 118.68, 123.45, 126.24, 126.75, 127.84, 130.26, 130.77, 147.11, 147.39, 149.47, 150.31, 151.96, 157.82, 174.07.

The above description and examples are not limitative of the invention, which is defined by the scope of the following claims.

What is claimed is:

1. A process for synthesizing a compound having the formula I:

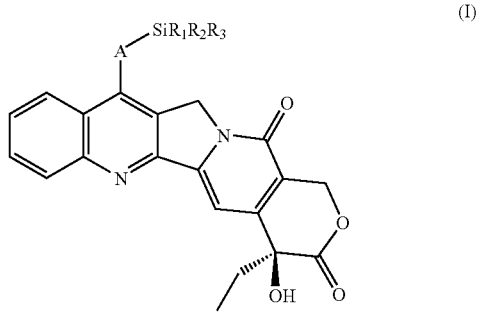

where A is —(CH$_2$)$_m$—;
m is 1 to 6; and R$_1$, R$_2$, and R$_3$ are individually lower alkyl or aryl substitutent groups; the process comprising:
a) providing a quantity of substantially pure camptothecin, and dissolving said camptothecin in a solution of a strong acid;
b) providing a quantity of a compound having the formula II: R$_3$R$_2$R$_1$Si—A$_m$—X (II),
wherein X is 1,3-dioxolane and dissolving II in an organic-based solution; and
c) mixing the solutions from steps a) and b) for a sufficient period of time to allow them to react to form the formula I compound.

2. The process of claim 1, wherein the strong acid is sulfuric acid, and the organic-based solution is a lower alcohol or benzyl alcohol.

3. The process of claim 1, wherein step a) includes adding a quantity of a metal hydrate catalyst and a strong oxidizing agent to the strong acid solution.

4. The process of claim 1 wherein R$_1$, R$_2$ and R$_3$ are methyl.

5. The process of claim 3, wherein the metal hydrate is ferrous sulfate and the strong oxidizing agent is hydrogen peroxide.

6. The process of claim 1, wherein m is 1 to 4, and each of R$_1$, R$_2$ and R$_3$ is individually a methyl, tert-butyl or phenyl substituent group.

7. The process of claim 1, wherein m is 1 and each of R$_1$, R$_2$ and R$_3$ is a methyl substituent group.

* * * * *